US00PP35270P2

(12) United States Plant Patent
van Sambeek

(10) Patent No.: US PP35,270 P2
(45) Date of Patent: Jul. 18, 2023

(54) ***PEROVSKIA* PLANT NAMED 'DOPERJEL'**

(50) Latin Name: *Perovskia atriplicifolia*
Varietal Denomination: Doperjel

(71) Applicant: DUMMEN GROUP B.V., De Lier (NL)

(72) Inventor: Ellen van Sambeek, Oegstgeest (NL)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 17/991,568

(22) Filed: Nov. 21, 2022

(51) Int. Cl.
*A01H 5/02* (2018.01)
*A01H 6/50* (2018.01)

(52) U.S. Cl.
USPC ..... Plt./263.1

(58) Field of Classification Search
USPC ..... Plt./263.1
See application file for complete search history.

(56) References Cited

U.S. PATENT DOCUMENTS

PP25,581 P2 * 5/2015 Catt ..... A01H 5/02
Plt./263.1

* cited by examiner

*Primary Examiner* — Karen M Redden
(74) *Attorney, Agent, or Firm* — C. Anne Whealy

(57) ABSTRACT

A new and distinct cultivar of *Perovskia* plant named 'Doperjel', characterized by its relatively compact, upright to outwardly spreading plant habit; moderately vigorous growth habit; freely branching growth habit; freely flowering habit; small violet-colored bilabiate flowers arranged in verticillasters on long terminal spikes; and good garden performance.

2 Drawing Sheets

Figure 1:
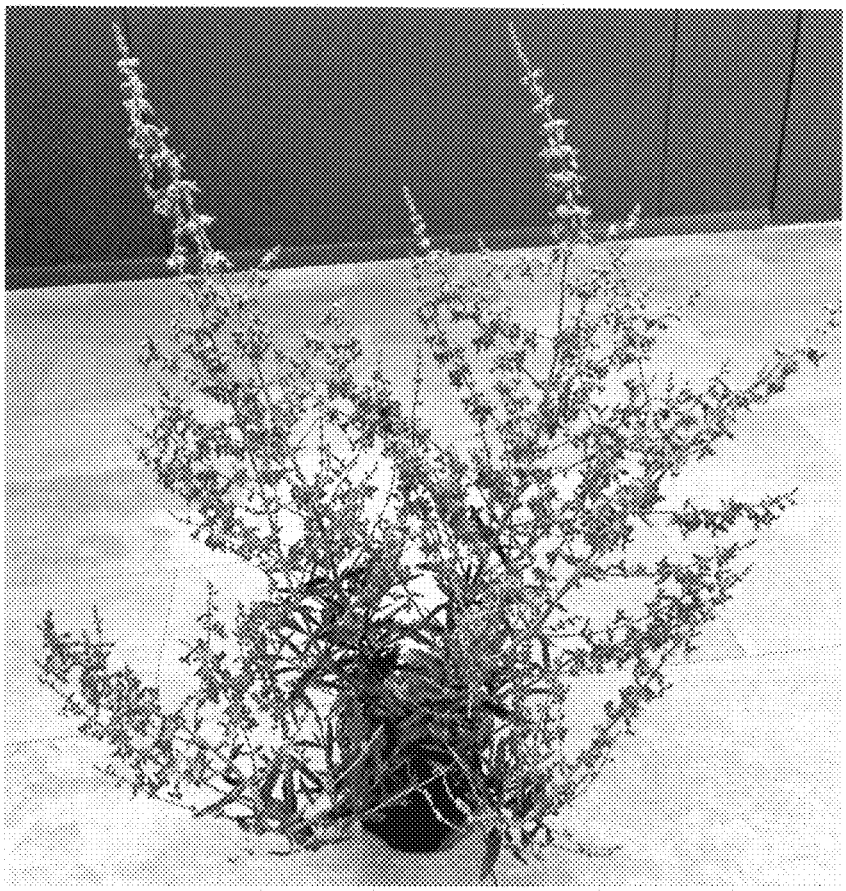

Botanical designation: *Perovskia atriplicifolia.*
Cultivar denomination: 'DOPERJEL'.

BACKGROUND OF THE INVENTION

The present invention relates to a new and distinct *Perovskia* plant, botanically known as *Perovskia atriplicifolia*, and hereinafter referred to by the name 'Doperjel'.

The new *Perovskia* plant is a product of a planned breeding program conducted by the Inventor in Aalsmeer, The Netherlands. The objective of the breeding program was to develop new unique *Perovskia* plants with attractive plant form and flower coloration.

The new *Perovskia* plant originated from an open-pollination in April, 2016 of a proprietary selection of *Perovskia atriplicifolia* identified as code number PV16-000022-002, not patented, as the female, or seed, parent with an unknown selection of *Perovskia atriplicifolia* as the male, or pollen, parent. The new *Perovskia* plant was discovered and selected by the Inventor as a single flowering plant within the progeny of the stated open-pollination in a controlled environment in Aalsmeer, The Netherlands in July, 2017.

Asexual reproduction of the new *Perovskia* plant by terminal cuttings in a controlled greenhouse environment in Aalsmeer, The Netherlands since August, 2017 has shown that the unique features of this new *Perovskia* plant are stable and reproduced true to type in successive generations.

SUMMARY OF THE INVENTION

Plants of the new *Perovskia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Perovskia* plant. These characteristics in combination distinguish 'Doperjel' as a new and distinct *Perovskia* plant:

1. Relatively compact, upright to outwardly spreading plant habit.
2. Moderately vigorous growth habit.
3. Freely branching growth habit.
4. Freely flowering habit.
5. Small violet-colored bilabiate flowers arranged in verticillasters on long terminal spikes.
6. Good garden performance.

Plants of the new *Perovskia* differ primarily from plants of the female parent selection in plant habit as plants of the new *Perovskia* are shorter and more compact than plants of the female parent selection.

Plants of the new *Perovskia* can be compared to plants of the *Perovskia hybrida* 'Little Spire', disclosed in U.S. Plant Pat. No. 11,643. In side-by-side comparisons, plants of the new *Perovskia* differ primarily from plants of 'Little Spire' in plant size as plants of the new *Perovskia* are shorter and more compact than plants of 'Little Spire'. In addition, plants of the new *Perovskia* are more freely branching than plants of 'Little Spire'.

BRIEF DESCRIPTION OF THE PHOTOGRAPHS

The accompanying photographs illustrate the overall appearance of the new *Perovskia* plant showing the colors as true as it is reasonably possible to obtain in colored reproductions of this type. Colors in the photographs may differ slightly from the color values cited in the detailed botanical desription which accurately describe the colors of the new *Perovskia* plant.

The photograph on the first sheet (FIG. 1) is a side perspective view of a typical flowering plant of 'Doperjel' grown in a container.

Figure 2:
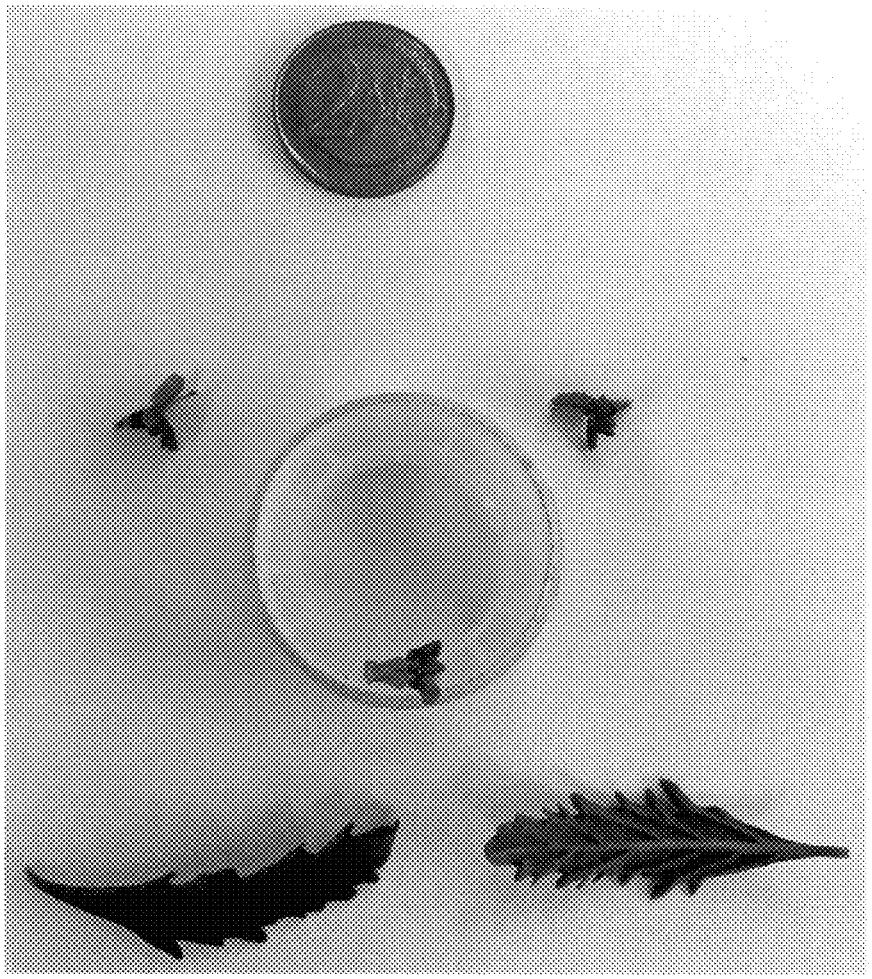

The photograph on the second sheet (FIG. 2) are close-up views of typical leaves and flowers of 'Doperjel'.

DETAILED BOTANICAL DESCRIPTION

The aforementioned photographs and following observations and measurements describe plants grown in 13-cm containers in Straelen, Germany during the early summer in an outdoor nursery and under conditions and cultural practices which approximate those generally used in commercial *Perovskia* plant production. During the production of the plants, day temperatures averaged 21° C. and night temperatures averaged 15° C. Plants were pinched two weeks after planting rooted young plants and were 18 weeks old when the photographs and description were taken. In the following description, color references are made to The Royal Horticultural Society Colour Chart, Fifth Edition, except where general terms of ordinary dictionary significance are used.

Botanical classification: *Perovskia atriplicifolia* 'Doperjel'.

Parentage:

*Female, or seed, parent.*—Proprietary selection of *Perovskia atriplicifolia* identified as code number PV16-000022-002, not patented.

*Male, or pollen, parent.*—Unknown selection of *Perovskia atriplicifolia*, not patented.

Propagation:

*Type.*—Terminal vegetative cuttings.

*Time to initiate roots, summer.*—About 16 days at temperatures about 26° C.

*Time to initiate roots, winter.*—About three weeks at temperatures about 23° C.

*Time to produce a rooted young plant, summer.*—About 24 days at temperatures about 23° C.

*Time to produce a rooted young plant, winter.*—About four weeks at temperatures about 18° C.

*Root description.*—Medium in thickness, fibrous; typically white to light yellow in color, actual color of the roots is dependent on substrate composition, water quality, fertilizer type and formulation.

*Rooting habit.*—Moderately freely branching; medium density.

Plant description:

*Plant and growth habit.*—Herbaceous perennial; relatively compact, upright to outwardly spreading plant habit; freely branching habit; moderately vigorous growth habit and moderate growth rate; bilabiate flowers arranged in verticillasters on long terminal spikes.

*Plant height, soil level to top of foliar plane.*—About 30 cm.

*Plant height, soil level to top of floral plane.*—About 58 cm.

*Plant width.*—About 41 cm.

*Lateral branch description.*—Quantity per plant: Freely branching habit with about seven secondary lateral branches developing per plant. Length: About 50 cm. Diameter: About 4 mm. Internode length: About 3 cm. Strength: Strong. Aspect: About 20° to 60° from vertical. Texture and luster: Smooth, glabrous; semi-glossy. Color, when developing and developed: Close to 138A; if woody, close to 200C.

*Leaf description.*—Arrangement: Opposite and decussate, simple. Length: About 5.1 cm. Width: About 1.5 cm. Shape: Lanceolate. Apex: Acute. Base: Acuminate. Margin: Serrate with shallow divergent identations. Texture and luster, upper surface: Smooth, glabrous; semi-glossy. Texture and luster, lower surface: Smooth, glabrous; glossy. Venation pattern: Pinnate and reticulate. Color: Developing leaves, upper surface: Close to 137A. Developing leaves, lower surface: Close to 137B. Fully expanded leaves, upper surface: Close to 137B; venation, close to 137B. Fully expanded leaves, lower surface: Close to 137C; venation, close to 137D. Petioles: Length: About 4 mm. Diameter: About 1 mm. Strength: Moderately strong. Texture and luster, upper and lower surfaces: Smooth, glabrous; glossy. Color, upper and lower surfaces: Close to 144A.

Flower description:

*Flower type, arrangement and habit.*—Single bilabiate flowers arranged in verticillasters on long terminal spikes; freely flowering, about 35 flowers developing per inflorescence and about 2,060 flowers developing per plant during the flowering season; flowers with two-lobed upper lip and three-lobed lower lip; flowers face mostly outwardly on the spike; flowers sessile.

*Natural flowering season.*—Flowering is continuous in July and August in Germany and in The Netherlands; early flowering habit, plants begin flowering about 18 weeks after planting.

*Flower longevity on the plant.*—Inflorescences last about three to four weeks on the plant; flowers not persistent.

*Fragrance.*—Strongly fragrant; pleasant.

*Flower buds.*—Length: About 4 mm. Diameter: About 2 mm. Shape: Elliptic. Texture and luster: Pubescent; matte. Color: Close to 90A.

*Inflorescence size.*—Height: About 24 cm. Diameter: About 3 cm.

*Flower size.*—Diameter: About 8 mm by 9 mm. Depth (height): About 8 mm. Throat diameter: About 2 mm. Tube length: About 5 mm. Tube diameter: About 2 mm.

*Petals.*—Quantity and arrangement: Upper lip, two-lobed and lower lip, three-lobed; proximally fused. Length: About 6 mm. Width: About 4 mm. Shape: Lower lip, linear; upper lip, three-lobed. Apex: Lower lip, obtuse; upper lip, three-lobed. Margin: Entire; moderately undulate. Texture and luster, upper and lower surfaces: Smooth, glabrous; matte. Texture, throat and tube: Smooth, glabrous; matte. Color: When opening and fully opened, upper surface: Close to 93B; venation, close to 93B; color becoming closer to 93A with subsequent development. When opening and fully opened, lower surface: Close to 93C; venation, close to 93C; color becoming closer to 93A with subsequent development. Throat: Close to 93B; venation, close to 93B. Tube: Close to 93C; venation, close to 93C.

*Calyx.*—Arrangement: Four sepals fused forming a bilabiate calyx. Length: About 5 mm. Diameter: About 2 mm. Sepal length: About 5 mm. Sepal diameter: About 1 mm. Sepal apex: Acute. Sepal margin, free-part: Entire. Sepal texture and luster, upper surface: Pubescent; matte. Sepal texture and luster, lower surface: Smooth, glabrous; matte. Sepal color: When opening and fully opened, upper surface: Close to 90A. When opening and fully opened, lower surface: Close to N137A.

*Peduncles.*—Length: About 6 cm. Diameter: About 2 mm. Aspect: About 45° from lateral branch axis. Strength: Moderately strong. Texture and luster: Smooth, glabrous; semi-glossy. Color: Close to 138B.

*Reproductive organs.*—Stamens: Quantity per flower: Two. Filament length: About 2 mm. Filament color: Close to 93C. Anther shape: Rounded; dorsifixed. Anther size: About 1 mm by 1 mm. Anther color: Close to 95C. Pollen amount: Scarce. Pollen color: Close to NN155D. Pistils: Quantity per flower: One. Pistil length: About 1.2 cm. Stigma shape: Bifid. Stigma diameter: About 1 mm. Stigma color: Close to 93B. Style length: About 9 mm. Style color: Close to 93C. Ovary color: Close to 144A.

*Seeds and fruits.*—To date, seed and fruit production has not been observed on plants of the new *Perovskia.*

Pathogen & pest resistance: To date, plants of the new *Perovskia* have not been noted to be resistant to pathogens and pests common to *Perovskia* plants.

Garden performance: Plants of the new *Perovskia* have exhibited good tolerance to rain, wind and to tolerate temperatures ranging from −30° C. to about 30° C. and to be suitable for USDA Hardiness Zones 3 through 9.

It is claimed:

1. A new and distinct *Perovskia* plant named 'Doperjel' as illustrated and described.

* * * * *